United States Patent
Kim et al.

(10) Patent No.: US 9,358,190 B2
(45) Date of Patent: Jun. 7, 2016

(54) DYEING COMPOSITION

(71) Applicants: Jong Hyub Kim, Yongin-si (KR); Jae Jung Park, Yongin-si (KR); Hyo Seung Moon, Yongin-si (KR); Jang Won Choi, Yongin-si (KR); Wang Gi Kim, Yongin-si (KR)

(72) Inventors: Jong Hyub Kim, Yongin-si (KR); Jae Jung Park, Yongin-si (KR); Hyo Seung Moon, Yongin-si (KR); Jang Won Choi, Yongin-si (KR); Wang Gi Kim, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/357,378

(22) PCT Filed: Nov. 16, 2012

(86) PCT No.: PCT/KR2012/009737
§ 371 (c)(1),
(2) Date: May 9, 2014

(87) PCT Pub. No.: WO2013/073893
PCT Pub. Date: May 23, 2013

(65) Prior Publication Data
US 2014/0338135 A1    Nov. 20, 2014

(30) Foreign Application Priority Data

Nov. 16, 2011 (KR) .................. 10-2011-0119495
Nov. 15, 2012 (KR) .................. 10-2012-0129207

(51) Int. Cl.
*A61Q 5/10* (2006.01)
*A61K 8/33* (2006.01)
*A61K 8/34* (2006.01)
*A61K 8/39* (2006.01)
*A61K 8/86* (2006.01)

(52) U.S. Cl.
CPC ... *A61K 8/33* (2013.01); *A61K 8/34* (2013.01); *A61K 8/342* (2013.01); *A61K 8/39* (2013.01); *A61K 8/86* (2013.01); *A61Q 5/10* (2013.01)

(58) Field of Classification Search
CPC ............. A61Q 5/10; A61K 8/34; A61K 8/37; A61K 8/39; A61K 8/86
USPC ............. 8/405, 406, 408, 497, 552, 580, 609, 8/611
See application file for complete search history.

(56) References Cited

U.S. PATENT DOCUMENTS 6,916,432 B2 *   7/2005   Matsuo et al. ............. 252/186.1
7,842,101 B2 *  11/2010   Matsunaga et al. ............... 8/405

(Continued)

FOREIGN PATENT DOCUMENTS

JP         06183934 A      7/1994
KR      1020050019735 A    3/2005

(Continued)

OTHER PUBLICATIONS

International Search Report for International Application No. PCT/KR2012/009737 dated Mar. 25, 2013.

(Continued)

*Primary Examiner* — Eisa Elhilo
(74) *Attorney, Agent, or Firm* — Cantor Colburn LLP (57) ABSTRACT

The present invention relates to a dyeing composition. More particularly, the present invention provides a dyeing composition comprising an ether-based nonionic surfactant, an ether-based oil and alcohol. Preferably, the ether-based nonionic surfactant, the ether-based oil and the alcohol have the same number of carbon atoms. The dyeing composition according to the present invention comprises the ether-based nonionic surfactant, the ether-based oil and the alcohol, forms a multi-lamellar liquid crystal structure, allows for ease of material application and maintains excellent color formation, and particularly, mitigates pungent smell, eye irritation and the like.

10 Claims, 3 Drawing Sheets

(56) References Cited

U.S. PATENT DOCUMENTS

| | | |
|---|---|---|
| 2005/0076459 A1* | 4/2005 | Guardia et al. .................. 8/405 |
| 2005/0166337 A1* | 8/2005 | Adam et al. ..................... 8/406 |
| 2006/0042023 A1 | 3/2006 | Machida |

FOREIGN PATENT DOCUMENTS

| | | |
|---|---|---|
| KR | 1020050074860 A | 7/2005 |
| KR | 1020060057664 | 5/2006 |
| KR | 1006635930000 B1 | 12/2006 |
| KR | 1020070029746 A | 3/2007 |
| KR | 100757028 B1 | 9/2007 |

OTHER PUBLICATIONS

Written Opinion for International Application No. PCT/KR2012/009737 dated Mar. 25, 2013.

* cited by examiner

DYEING COMPOSITION

TECHNICAL FIELD

The present disclosure relates to a dyeing composition, and more particularly to a dyeing composition comprising an ether type nonionic surfactant and ether type oil having the same carbon number and an alcohol having the same carbon number as the surfactant and oil, and thus having excellent color formability while causing a reduced pungent smell and eye-smarting.

BACKGROUND ART

Keratin fibers including human hair may be colored (dyed) by the oxidative condensation reaction of a dyeing composition, particularly oxidative dyeing composition. In general, as described in Korean Patent Publication No. 10-0757028 or the like, such a dyeing composition comprises a first part containing an oxidative dye precursor, coupler and an alkaline agent, and a second part containing an oxidizing agent, and the two parts are mixed with each other upon use.

The oxidative dye precursor and coupler infiltrate into hair and are coupled with each other via oxidative condensation, resulting in color formation. During such color formation, the alkaline agent (e.g. ammonia) contained in the first part accelerates the formation of perhydroxy anions of the oxidizing agent (e.g. hydrogen peroxide), and the perhydroxy anions cause the oxidation of a dye and melanin decomposition, resulting in color formation and decoloration.

However, although the perhydroxy anions of the oxidizing agent serve to carry out the oxidation of a dye and melanin decomposition, the oxidative agent molecules may react among themselves as undesired side reaction to form radicals, which, in turn, may cause decomposition of hair proteins, leading to hair damages, comprising degradation of hair gloss and color formability. In addition, ammonia is used typically as an alkaline agent contained in the first part to accelerate the oxidation. However, such an alkaline agent having volatility is problematic in that it causes generation of a pungent smell. Further, such an alkaline agent increases pH, thereby causing scalp irritation and eye-smarting.

To solve the above-mentioned problems, many approaches have been suggested. For example, Korean Patent Laid-Open No. 10-2005-0074860 discloses a method for enhancing color formability by using a phosphate surfactant capable of forming a multi-lamella liquid crystal structure and inducing a delay in reaction between the oxidative dye precursor and the coupler. However, the method suggests no solution to the problems of a pungent smell caused by the alkaline agent and sulfur compounds as well as eye-smarting.

Referring to the above-mentioned pungent smell and eye-smarting, when an alkaline agent present in an aqueous phase (continuous phase) is allowed to be in an inner phase of micelles, vesicles or emulsion, or when the emulsion is provided with very high viscosity, it is possible to reduce a pungent smell and eye-smarting.

However, in the case of a W/O formulation having an aqueous phase (continuous phase) as an inner phase of micelles, a dye co-existing with the aqueous phase is present in the inner phase at the same time, thereby making it difficult to carry out mass transfer (adhesion) to the hair, resulting in degradability of color formability. In addition, when the emulsion has very high viscosity, it cannot be applied to the hair with ease and the mass transfer is also difficult in this case, resulting in degradation of color formability.

REFERENCES

Patent Documents (Patent Document 1) Korean Patent Publication No. 10-0757028

(Patent Document 2) Korean Patent Laid-Open No. 10-2005-0074860

DISCLOSURE

Technical Problem

A technical problem to be solved by the present disclosure is to provide a dyeing composition that facilitates the mass transfer to keratin fibers such as hair and reduces a pungent smell and eye-smarting while maintaining excellent color formability.

Technical Solution

In one general aspect, there is provided a dyeing composition, comprising:
an ether type nonionic surfactant;
ether type oil; and
an alcohol.

According to an embodiment, the ether type nonionic surfactant, ether type oil and alcohol have the same carbon number.

According to another embodiment, the ether type nonionic surfactant is selected from ethylene oxide-containing surfactants, and particularly comprises at least two surfactants having a different ethylene oxide mole number.

According to still another embodiment, the ether type nonionic surfactant comprises at least two surfactants, and preferably comprises a surfactant having an HLB less than 10 and another surfactant having an HLB of 10 or more.

According to still another embodiment, the ether type nonionic surfactant is selected from polyethylene oxide alkyl ethers, and the ether oil is selected from polypropylene oxide alkyl ethers.

Advantageous Effects

According to the embodiments of the present disclosure, the dyeing composition comprising an ether type nonionic surfactant, ether type oil and an alcohol forms a multi-lamella liquid crystal structure and facilitates the mass transfer to keratin fibers such as hair, and thus improves the problems of a pungent smell and dye-smarting while maintaining excellent color formability.

In addition, the dyeing composition forms a stable three-dimensional lamella structure to improve the stability of composition and enhance the compatibility of a gas for use in providing an aerosol type formulation.

BEST MODE

Hereinafter, the present disclosure will be explained in detail.

The dyeing composition according to the present disclosure may be provided as an oxidative dyeing composition that comprises a first part and a second part like the conventional dyeing composition and is used by mixing the first part with the second part. Particularly, the first part may comprise an oxidative dye precursor, coupler and an alkaline agent, and the second part may comprise an oxidizing agent.

In addition, the dyeing composition further comprises an ether type nonionic surfactant, ether type oil and an alcohol. Preferably, the ether type nonionic surfactant, ether type oil and the alcohol have the same carbon number. Particularly, the ether type nonionic surfactant, ether type oil and the alcohol preferably have a carbon chain having the same carbon number.

The ether type nonionic surfactant, ether type oil and the alcohol may be comprised to at least one selected from the first part and the second part. Particularly, the dyeing composition according to the present disclosure comprises an ether type nonionic surfactant, ether type oil and an alcohol, and all of the three ingredients may be comprised to the first part or to the second part. In addition, all of the three ingredients may be comprised to the second part as well as the first part. Further, at least one of the three ingredients may be comprised to the first part, and the others may be comprised to the second part. In other words, the three ingredients used in the dyeing composition according to the present disclosure are partially or totally comprised to at least one part selected from the first part and the second part, so that the final dyeing composition may comprise all of the three ingredients upon use. Preferably, at least one part selected from the first part and the second part comprise all of the three ingredients.

The three ingredients, i.e., the ether type nonionic surfactant, ether type oil and the alcohol preferably have the same carbon number as described above. The three ingredients have a carbon chain, such as alkyl group or aryl group, having the same carbon number. More particularly, the ether type nonionic surfactant and ether type oil are selected from ether type compounds having an alkyl group in the backbone as a carbon chain having the same carbon number. In addition, the alcohol may be selected from higher alcohols having an alkyl or aryl group in the backbone as a carbon chain having the same carbon number.

The ether type nonionic surfactant is selected from ether type compounds containing a carbon chain having the same carbon number as the ether type oil and alcohol. Preferably, the ether type nonionic surfactant is selected from surfactants having ethylene oxide (EO) in their molecules. Herein, the ether type nonionic surfactant comprises at least two surfactants having ethylene oxide (EO), particularly at least two surfactants having a different ethylene oxide (EO) mole number. When using at least two surfactants having a different ethylene oxide (EO) mole number, formation of a multi-lamella liquid crystal structure is facilitated and color formability is improved in addition to improvement in a pungent smell and eye-smarting.

According to a preferred embodiment, the ether type nonionic surfactant is a polyethylene oxide alkyl ether. In addition, at least two polyethylene oxide alkyl ethers having a different ethylene oxide (EO) mole number are used preferably. For example, a polyethylene oxide stearyl ether having an ethylene oxide (EO) mole number equal to or more than 0.2 moles and less than 10 moles may be used together with another polyethylene oxide stearyl ether having an ethylene oxide (EO) mole number of 10 moles or more and 40 moles or less.

In addition, the ether type nonionic surfactant may comprise at least two surfactants containing a carbon chain having the same carbon number as the ether oil and alcohol, particularly a surfactant having an Hydrophilie Lipophile Balance (HLB) less than 10 and another surfactant having an HLB of 10 or more. In other words, at least two ether type nonionic surfactants are used, it is preferred that at least one of which has an HLB less than 10 and at least one of which has an HLB of 10 or more. For example, an ether type nonionic surfactant having an HLB equal to or more than 2 and less than 10 may be used in combination with another ether type nonionic surfactant having an HLB of 10-30. When the ether type nonionic surfactant comprises a surfactant having an HLB of 10 or less and another surfactant having an HLB of 10 or more, color formability is further improved in addition to improvement in a pungent smell and eye-smarting. Considering these, the ether type nonionic surfactant preferably comprises a surfactant having an HLB less than 10 and another surfactant having an HLB of 10 or more in a weight ratio of 2-2.5:1-1.5. In other words, the weight ratio of [surfactant having an HLB less than 10: surfactant having an HLB or 10 or more] is preferably 2-2.5:1-1.5.

In addition, the ether type oil may be selected from the compounds used as oil in the field of cosmetics or hair-dyeing agents. Such compounds may be used alone or in combination, as long as they belong to ether compounds having the same carbon number as the ether type nonionic surfactant and alcohol. Preferably, the ether type oil may be selected from polypropylene oxide alkyl ethers, and more particularly polypropylene oxide stearyl ethers.

Further, the alcohol may be selected from those used in the field of cosmetics and hair-dyeing agents. There is no particular limitation in alcohol, as long as it contains a carbon chain having the same carbon number as the ether type nonionic surfactant and ether type oil. The alcohol may be a higher alcohol, such as an aliphatic or aromatic alcohol having a carbon number of 12 or more. Particularly, the alcohol may be selected from C14-C22 higher alcohols. The alcohol may be at least one selected from cetyl alcohol and cetearyl alcohol, but is not limited thereto.

According to the present disclosure, the dyeing composition comprises the three ingredients, i.e., the ether type nonionic surfactant, ether type oil and the alcohol having the same carbon number, and the three ingredients form a multi-lamella liquid crystal structure and partially collect the dye, alkaline agent and the oxidizing agent (e.g. hydrogen peroxide) present in an aqueous phase. In other words, the three ingredients form O/W emulsion while allowing a part of aqueous phase to be distributed in the inner phase and outer phase of emulsion. Thus, it is possible to accelerate the decoloration of keratin fibers (hair) and infiltration of a dye into keratin fibers (hair), thereby providing excellent color formability. It is also possible to prevent instant evaporation of ammonia and sulfur compounds, thereby improving a pungent smell and eye-smarting.

Particularly, the ether type nonionic surfactant and alcohol (higher alcohol) having the same carbon number as the former are emulsified to form a film on which the ether type oil having the same carbon number is disposed, thereby forming a multilayer film (multi-lamella). As a result, the aqueous phase and the oil phase are disposed in a different layer in the multi-lamella structure. Thus, according to the present disclosure, it is possible to improve the adhesion to keratin fibers (hair) and to maintain excellent color formability, while causing a reduced pungent smell and eye-smarting by preventing the evaporation of pungent materials.

In addition, by virtue of such a three-dimensional lamella structure having multiple layers, the dyeing composition itself has improved stability. Further, when preparing an aerosol type formulation according to an embodiment, it is possible to incorporate a liquefying gas that liquefies under the internal pressure to the inner phase most efficiently as a spraying agent filled in the aerosol, thereby enhancing the compatibility of liquefying gas effectively. Particular examples of the liquefying gas may comprise LPG gases, such as propane gas, butane gas and mixed propane/butane gas, and dimethyl ether (DME), but is not limited thereto. In addition, when preparing an aerosol type formulation, the composition and spraying agent may be controlled in amount depending on viscosity and spraying degree in a container. For example, the composition may be mixed with LPG (propane:butane=30:70) in a weight ratio of 70-98:30-2, 80-95:20-5, 90-95:10-5, or the like.

Further, although there is no particular limitation, the ether type nonionic surfactant may be used in an amount of 0.01-30 wt % based on the total weight of the dyeing composition according to the present disclosure. In addition, the ether type oil may be used in an amount of 0.01-30 wt % based on the total weight of the dyeing composition according to the present disclosure, and the alcohol (higher alcohol) may be used in an amount of 0.01-30 wt % based on the total weight of the dyeing composition according to the present disclosure. When the dyeing composition comprises the three ingredients within the above-defined ranges, the color formability, pungent smell and eye-smarting are improved desirably.

According to a preferred embodiment, the dyeing composition according to the present disclosure may further comprise a phosphate surfactant as an additional ingredient for improving color formability, in addition to the above-mentioned three ingredients. When such an additional phosphate surfactant is used, it is possible to further improve the color formability. Preferably, the phosphate surfactant is at least one selected from alkyl phosphate esters and alkoxylated phosphate esters. When such a surfactant is used, it is possible to further enhance the color formability. Although there is no particular limitation, the phosphate surfactant may be used in an amount of 0.01-20 wt % based on the total weight of the dyeing composition according to the present disclosure. Further, the phosphate surfactant may be comprised in at least one selected from the first part and the second part.

As described above, the dyeing composition according to the present disclosure preferably comprises a first part containing an oxidative dye precursor, coupler and an alkaline agent, and a second part containing an oxidizing agent, wherein the ether type nonionic surfactant, ether type oil and the alcohol have the same carbon number. More preferably, the dyeing composition further comprises a phosphate surfactant as mentioned above. In addition, the dyeing composition may be neutral or alkaline, and particularly has a pH of 7-12.

The oxidative dye precursor, coupler, alkaline agent and the oxidizing agent are not limited particularly, and those used currently in the art may be used.

Particular examples of the oxidative dye precursor comprise at least one selected from the group consisting of o-aminophenol, p-aminophenol, toluene-2,5-diamine hydrochloride, p-phenylene diamine hydrochloride, toluene-2,5-diamine, p-phenylene diamine sulfate, p-methylaminophenol sulfate, o-aminophenol sulfate, p-aminophenol sulfate, toluene-2,5-diamine sulfate and p-phenylene diamine sulfate. Preferably, at least two selected from the above-listed compounds may be used as the oxidative dye precursor. In addition, according to an embodiment, the oxidative dye precursor may be used in an amount of 0.001-5.0 wt % based on the total weight of the first part composition.

The coupler may be one capable of providing various color tones to hair when used in combination with the oxidative dye precursor. Although there is no particular limitation, the coupler may be at least one selected from the group consisting of 2-methyl-5-hydroxyethyl aminophenol, p-amino-o-cresol, m-aminophenol, 2,4-diaminophenoxyethanol hydrochloride, m-phenylenediamine hydrochloride, m-phenylenediamine, α-naphthol, resorcinol and 2-methylresorcinol. Preferably, the coupler may be at least two selected from the above-listed compounds. In addition, according to an embodiment, the coupler may be used in an amount of 0.001-5.0 wt % based on the total weight of the first part composition.

The alkaline agent may be the conventional alkaline material. For example, the alkaline agent may be at least one selected from the group consisting of ammonia, monoethanolamine, arginine, aminomethylpropanol, isopropanolamine, sodium hydroxide and potassium hydroxide. Further, the alkaline agent may be incorporated to the first part as aqueous solution and used without detracting from the effect of the present disclosure. According to an embodiment, the alkaline agent may be used in an amount of 0.1-10.0 wt % based on the total weight of the first part composition. For example, when the alkaline agent is aqueous ammonia having a concentration of 25-30 wt %, it may be used in an amount of 0.5-40 wt % based on the total weight of the first part composition.

The oxidizing agent is not particularly limited as long as it is capable of oxidizing the oxidative dye precursor. For example, the oxidizing agent may be at least one selected from the group consisting of hydrogen peroxide, urea peroxide, alkaline metal bromate, ferricyanide, perborate and persulfate. Preferably, the oxidizing agent is hydrogen peroxide and may be incorporated to the second part as aqueous solution. Further, according to an embodiment, the oxidizing agent may be used in an amount of 0.1-10.0 wt % based on the total weight of the second part composition. In addition, when the oxidizing agent is aqueous hydrogen peroxide having a concentration of 35 wt %, it may be used in an amount of 0.3-30 wt % based on the total weight of the second part composition.

In addition, the dyeing composition according to the present disclosure may further comprise a currently used direct dye without departing from the purpose of the present disclosure. For example, such a direct dye may be selected from the group consisting of Arianol dye, p-nitro-o-phenylenediamine, nitro-p-phenylenediamine, 2-amino-4-nitrophenol, 2-amino-5-nitrophenol, nitro-p-phenylenediamine hydrochloride, picramic acid and other vegetable dyes such as Henna.

The dyeing composition according to the present disclosure may further comprise other ingredients and additives used conventionally in hair-dyeing agents. For example, the dyeing composition may further comprise an antioxidizing agent, chelating agent, solvent, surfactant, thickening agent, fragrance and a conditioning agent, which may be selected from those used conventionally in hair-dyeing agents. In addition, such ingredients and additives may be comprised to the first part.

For example, the antioxidizing agent may comprise butylhydroxyanisole, dibutylhydroxytoluene, tert-butylhydroquinone and tocophenols. The chelating agent may comprise EDTA, sodium-EDTA (Na-EDTA) and pentasodium pentetate. The solvent may comprise ethanol, propyl alcohol, isopropyl alcohol, propylene glycol, hexylene glycol and diethylene glycol. In addition, the surfactant may comprise conventional cationic surfactants, anionic surfactants or nonionic surfactants. The thickening agent may comprise higher alcohols, nonionic polymers and anionic polymers. The conditioning agent may comprise cationic polymers, quaternized ammonium salts and silicone.

In addition, the second part may further comprise other ingredients used conventionally in hair-dyeing agents without detracting from the effect of the present disclosure. Although there is no particular limitation, the second part may further comprise at least one ingredient selected from the group consisting of: fats and oil, such as paraffin, hard liquid isoparaffin, higher fatty alcohols and higher fatty acid esters; cationic and/or nonionic surfactants; stabilizers such as phenacetin; and pH modifiers such as phosphoric acid.

The dyeing composition according to the present disclosure further comprises water in the first part and/or the second part as usual, in addition to the above-described ingredients. Preferably, water that may be used herein comprises purified water such as ion exchange water and distilled water. The content of water is not limited particularly, as long as it is sufficient to dissolve or disperse the above ingredients.

The dyeing composition may be provided any formulation suitable for local application. For example, the dyeing composition may be provided in the form of a solution, emulsion, cream, suspension, solid, gel, powder, paste, foam or aerosol formulation. Such formulations may be prepared by any methods generally known to those skilled in the art.

As described above, the dyeing composition according to the present disclosure is useful for color formation (dyeing) of keratin fibers. More particularly, the dyeing composition is useful as a hair-dyeing agent applied to human hair. In addition, the dyeing composition may be used in the conventional manner. Particularly, the first part is mixed with the second part right before carrying out dyeing, the mixture is applied to hair, and the hair is washed after the lapse of a predetermined time.

Mode for Invention

Examples and Comparative Examples now will be described more fully hereinafter. The following Examples are for illustrative purposes only and provided to help those skilled in the art to understand the present disclosure. However, the scope of the present disclosure should not be construed as limited to the following Examples.

EXAMPLES AND COMPARATIVE EXAMPLES

Preparation Examples of First Part

A first part composition is prepared by using the ingredients and amounts thereof as shown in the following Table 1.

First, as aqueous phase, purified water, disodium EDTA (Na-EDTA), erythorbic acid, sodium sulfite, propylene glycol, a dye, or the like are introduced, warmed to 75° C. and dissolved. In addition, as oil phase, cetearyl alcohol, cetyl alcohol, mineral oil, polyethylene oxide stearyl ether, polypropylene oxide stearyl ether, dicetyl phosphate, Ceteth-20 phosphate, or the like are introduced, warmed to 75° C. and dissolved. As shown in Table 1, each preparation example uses different ingredients.

Next, the aqueous phase is mixed with the oil phase, followed by emulsification and cooling to 40° C. Then, strong aqueous ammonia (28 wt %) and a combined fragrance are further added thereto and mixed homogeneously to obtain a first part composition.

TABLE 1

<Ingredients and Amounts of First Part Composition>

| | Preparation Example of First Part (wt %) | | | | | | | |
|---|---|---|---|---|---|---|---|---|
| Ingredients | 1-1 | 1-2 | 1-3 | 1-4 | 1-5 | 1-6 | 1-7 | 1-8 |
| Cetearyl alcohol | 10.0 | 10.0 | 10.0 | 10.0 | 10.0 | 10.0 | 10.0 | 10.0 |
| Cetyl alcohol | 2.0 | 2.0 | 2.0 | 2.0 | 2.0 | 2.0 | 2.0 | 2.0 |
| Polyethylene oxide stearyl ether (EO: 2 mole) | 2.5 | 2.5 | 2.5 | 2.5 | 2.5 | 2.5 | — | — |
| Polyethylene oxide stearyl ether (EO: 21 mole) | 1.5 | 1.5 | 1.5 | 1.5 | 1.5 | 1.5 | 1.5 | 1.5 |
| Dicetyl phosphate | — | — | — | — | 1.0 | 1.0 | — | — |
| Ceteth-20 phosphate | — | — | — | — | 2.0 | 2.0 | — | — |
| Polypropylene oxide stearyl ether | 3.0 | 3.0 | — | — | 3.0 | 3.0 | — | — |
| Disodium EDTA | 0.2 | 0.2 | 0.2 | 0.2 | 0.2 | 0.2 | 0.2 | 0.2 |
| Erythorbic acid | 0.4 | 0.4 | 0.4 | 0.4 | 0.2 | 0.2 | 0.4 | 0.4 |
| Sodium sulfite | 0.4 | 0.4 | 0.4 | 0.4 | 0.4 | 0.4 | 0.4 | 0.4 |
| Propylene glycol | 2.0 | 2.0 | 2.0 | 2.0 | 0.2 | 0.2 | 2.0 | 2.0 |
| p-phenylene diamine | 0.3 | — | 0.3 | — | 0.3 | — | 0.3 | — |
| m-aminophenol | 0.3 | — | 0.3 | — | 0.3 | — | 0.3 | — |
| p-aminophenol | 0.3 | 0.3 | 0.3 | 0.3 | 0.3 | 0.3 | 0.3 | 0.3 |
| Resorcinol | 0.3 | 0.3 | 0.3 | 0.3 | 0.3 | 0.3 | 0.3 | 0.3 |
| Strong aqueous ammonia (28 wt %) | 5.0 | 10.0 | 5.0 | 10.0 | 10.0 | 10.0 | 5.0 | 10.0 |
| Combined fragrance | qsad | qsad | qsad | qsad | qsad | qsad | qsad | qsad |
| Purified water | to 100 | to 100 | to 100 | to 100 | to 100 | to 100 | to 100 | to 100 |

Preparation Example of Second Part

A second part composition is prepared by using the ingredients and amounts thereof as shown in the following Table 2.

First, as aqueous phase, purified water, disodium EDTA (Na-EDTA), sodium phosphate, phosphoric acid, sodium stannate, sodium lauryl sulfate, or the like are introduced, warmed to 75° C. and dissolved. In addition, as oil phase, cetearyl alcohol, cetyl alcohol, polyethylene oxide stearyl ether, polypropylene oxide stearyl ether, or the like are introduced, warmed to 75° C. and dissolved. As shown in Table 2, each preparation example uses different ingredients.

Next, the aqueous phase is mixed with the oil phase, followed by emulsification and cooling to 40° C. Then, aqueous hydrogen peroxide (35 wt %) is further added thereto and mixed homogeneously to obtain a second part composition.

TABLE 2

<Ingredients and Amounts of Second Part Composition>

| Ingredients | Preparation Example of Second Part (wt %) | |
|---|---|---|
| | 2-1 | 2-2 |
| Cetearyl alcohol | 2 | 2 |
| Cetyl alcohol | 2 | 2 |
| Polyethylene oxide stearyl ether (EO: 2 mole) | 1.5 | — |
| Polyethylene oxide stearyl ether (EO: 21 mole) | 1 | — |
| Polypropylene oxide stearyl ether | 2 | — |
| Sodium lauryl sulfate | — | 2.0 |
| Sodium stannate | 0.4 | 0.4 |
| Monosodium phosphate | 0.4 | 0.4 |
| Disodium EDTA | 0.2 | 0.2 |
| Phosphoric acid | 0.3 | 0.3 |
| Aqueous hydrogen peroxide (35 wt %) | 17.0 | 17.0 |
| Purified water | to 100 | to 100 |

Figure 1:
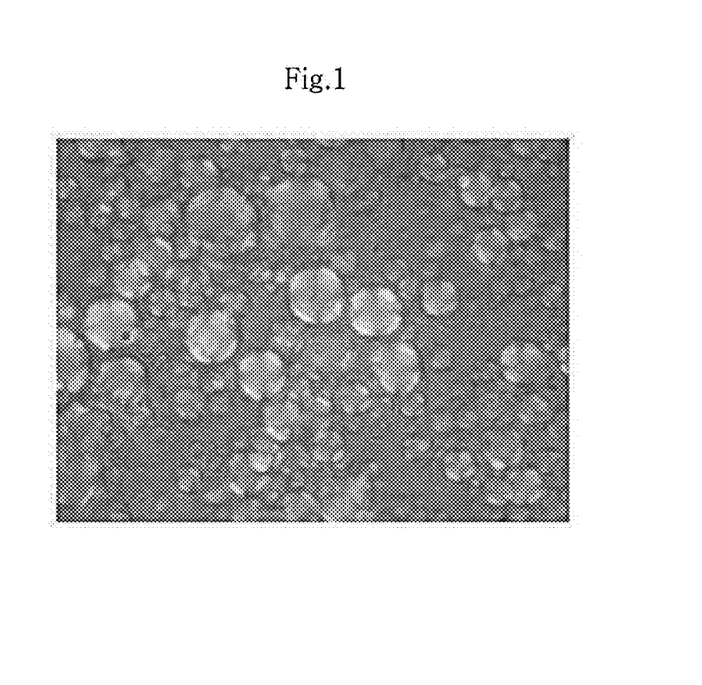
FIG. 1 to FIG. 4 are polarizing microscopic images (×100) of the first part of a dyeing composition according to an embodiment of the present disclosure.
Figure 2:
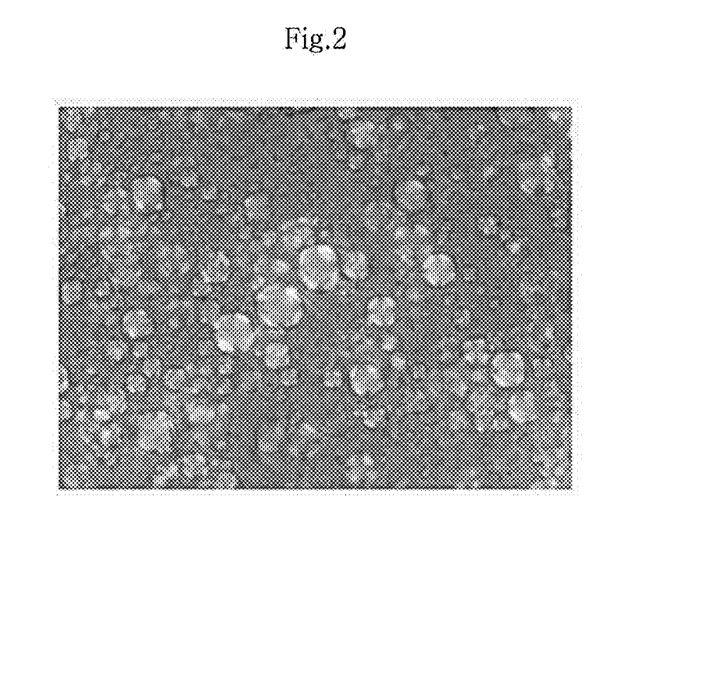
Figure 3:
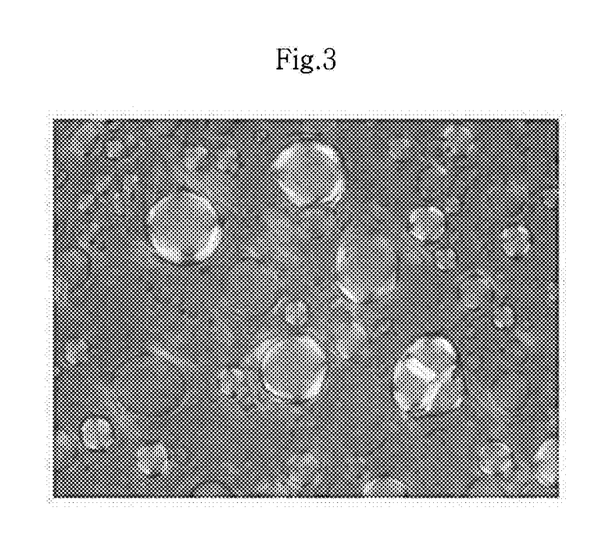
Figure 4:
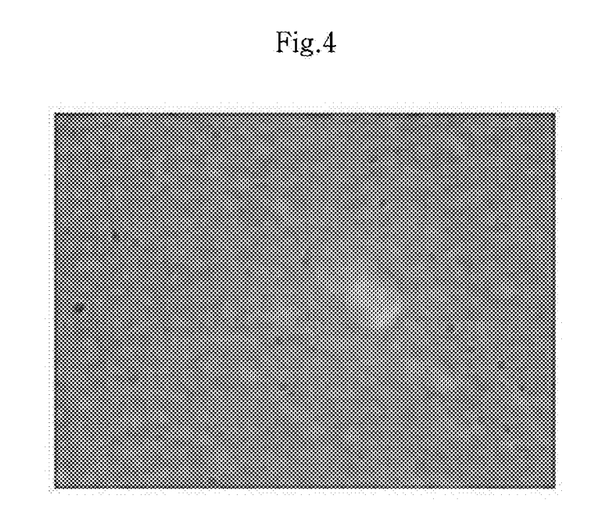

Meanwhile, FIG. 1 to FIG. 4 show polarizing microscopic images (×100) of the compositions (emulsions) according to the preparation examples of the first part as described above. FIG. 1 shows Preparation Example 1-1, FIG. 2 shows Preparation Example 1-3, FIG. 3 shows Preparation Example 1-5, and FIG. 4 shows Preparation Example 1-7.

As shown in FIG. 1 to FIG. 4, it can be seen that Preparation Example 1-1 (FIG. 1) and Preparation Example 1-5 (FIG. 3) comprising an ether type nonionic surfactant (polyethylene oxide stearyl ether), ether type oil (polypropylene oxide stearyl ether) and a higher alcohol (cetearyl alcohol, cetyl alcohol) having the same carbon number have a greater amount of multi-lamella liquid crystal structures with a larger size as compared to Preparation Example 1-3 (FIG. 2) and Preparation Example 1-7 (FIG. 4) not comprising the above three ingredients. In addition, it can be seen that Preparation Example 1-5 (FIG. 3) further comprising a phosphate surfactant has a greater amount of multi-lamella liquid crystal structures.

In addition, when comparing Preparation Example 1-3 (FIG. 2) to Preparation Example 1-7 (FIG. 4), Preparation Example 1-3 (FIG. 2) using two kinds of ether type nonionic surfactants (polyethylene oxide stearyl ether) having a different mole number of ethylene oxide (EO) shows a more distinct liquid crystal structure as compared to Preparation Example 1-7 (FIG. 4) not using such surfactants.

Therefore, it can be seen that the above three ingredients are mixed and emulsified in combination preferably to form a multi-lamella liquid crystal structure. In other words, it can be seen that when the above three ingredients are comprised totally to the first part or to the second part and emulsified, formation of a multi-lamella liquid crystal structure is facilitated. It can be also seen that at least two ether type nonionic surfactants having a different ethylene oxide (EO) mole number are used preferably.

Test Example 1

Evaluation of Color Formability

The first part and the second obtained from each Preparation Example are mixed in a weight ratio of 1:1. Herein, as shown in the following Table 3, a different first part and different second part are used in each Example and Comparative Example. Then, in order to evaluate the color formability of each oxidative dyeing composition according to each Example and Comparative Example, the resultant mixture of the first part with the second part is applied to black-colored human hair (black hair) for experiments right after the mixing, and allowed to stand for 30 minutes similarly to the conventional hair-dyeing agent. Then, the black hair is washed with a shampoo and dried. In addition, the color formability (coloring power) to hair after drying is evaluated by using the brightness values defined by a color-difference meter. The results are shown in the following Table 3. In Table 3, a lower brightness value (L) means higher color formability (coloring power).

TABLE 3

<Results of Evaluation of Color Formability (Brightness Values Defined by Color-Difference Meter)>

| | First Part + Second Part | Brightness Value (L) |
|---|---|---|
| Ex. 1 | Prep. Ex. 1-1 + Prep. Ex. 2-1 | 15.45 |
| Ex. 2 | Prep. Ex. 1-1 + Prep. Ex. 2-2 | 16.71 |
| Ex. 3 | Prep. Ex. 1-2 + Prep. Ex. 2-1 | 18.11 |
| Ex. 4 | Prep. Ex. 1-2 + Prep. Ex. 2-2 | 19.03 |
| Ex. 5 | Prep. Ex. 1-3 + Prep. Ex. 2-1 | 16.31 |
| Ex. 6 | Prep. Ex. 1-4 + Prep. Ex. 2-1 | 19.18 |
| Ex. 7 | Prep. Ex. 1-5 + Prep. Ex. 2-1 | 15.34 |
| Ex. 8 | Prep. Ex. 1-5 + Prep. Ex. 2-2 | 16.65 |
| Ex. 9 | Prep. Ex. 1-6 + Prep. Ex. 2-1 | 18.01 |
| Ex. 10 | Prep. Ex. 1-6 + Prep. Ex. 2-2 | 18.95 |
| Ex. 11 | Prep. Ex. 1-7 + Prep. Ex. 2-1 | 17.01 |
| Ex. 12 | Prep. Ex. 1-8 + Prep. Ex. 2-1 | 19.88 |
| Comp. Ex. 1 | Prep. Ex. 1-3 + Prep. Ex. 2-2 | 17.12 |
| Comp. Ex. 2 | Prep. Ex. 1-4 + Prep. Ex. 2-2 | 19.95 |
| Comp. Ex. 3 | Prep. Ex. 1-7 + Prep. Ex. 2-2 | 17.38 |
| Comp. Ex. 4 | Prep. Ex. 1-8 + Prep. Ex. 2-2 | 19.99 |

As shown in Table 3, Examples using an ether type nonionic surfactant (polyethylene oxide stearyl ether), ether type oil (polypropylene oxide stearyl ether) and a higher alcohol (cetearyl alcohol, cetyl alcohol) having the same carbon number provide higher color formability as compared to Comparative Examples not using at least one of the three ingredients. More particularly, Examples wherein the three ingredients are comprised to at least one part selected from the first part and the second part and the finally mixed composition has all of the three ingredients, it is possible to obtain higher color formability as compared to Comparative Examples not using at least one of the three ingredients.

For example, when comparing Example 5 (Prep. Ex. 1-3+ Prep. Ex. 2-1) to Comparative Example 1 (Prep. Ex. 1-3+

Prep. Ex. 2-2), Example 5 containing an ether type oil (polypropylene oxide stearyl ether) and the other same ingredients provides higher color formability as compared to Comparative Example 1 using no ether type oil (polypropylene oxide stearyl ether). The same is also applied to the comparison between Example 6 ((Prep. Ex. 1-4+Prep. Ex. 2-1) and Comparative Example 2 (Prep. Ex. 1-4+Prep. Ex. 2-2), and between Example 11 (Prep. Ex. 1-7+Prep. Ex. 2-1) and Comparative Example 3 (Prep. Ex. 1-7+Prep. Ex. 2-2).

In addition, it can be seen that use of an additional phosphate surfactant further improves color formability. For example, when comparing Example 1 (Prep. Ex. 1-1+Prep. Ex. 2-1) to Example 7 (Prep. Ex. 1-5+Prep. Ex. 2-1), Example 7 further comprising a phosphate surfactant (dicetyl phosphate, Ceteth-20 phosphate) provides higher color formability as compared to Example 1 using no phosphate surfactant. The same is also applied to the comparison between Example 3 (Prep. Ex. 1-2+Prep. Ex. 2-1) and Example 9 (Prep. Ex. 1-6+Prep. Ex. 2-1).

Further, it can be seen that Examples using two ether type nonionic surfactants (polyethylene oxide stearyl ether) having a different ethylene oxide (EO) mole number, it is possible to obtain higher color formability as compared to the other Examples not using such surfactants. For example, when comparing Example 5 (Prep. Ex. 1-3+Prep. Ex. 2-1) to Example 11 (Prep. Ex. 1-7+Prep. Ex. 2-1), Example 5 containing two ether type nonionic surfactants (polyethylene oxide stearyl ether) having a different ethylene oxide (EO) mole number and the other same ingredients provides higher color formability as compared to Example 11 using only one ether type nonionic surfactant (polyethylene oxide stearyl ether). The same is also applied to the comparison between Example 6 (Prep. Ex. 1-4+Prep. Ex. 2-1) and Example 12 (Prep. Ex. 1-8+Prep. Ex. 2-1).

Test Example 2

Evaluation of Pungent Smell and Eye-Smarting

To evaluate the degree of a pungent smell and eye-smarting caused by each oxidative dyeing composition according to Examples and Comparative Examples, the first part is mixed with the second part. After the lapse of 1 minute, five fragrance specialist panels evaluate each composition for the degree of a pungent smell and eye-smarting. The results are averaged and shown in the following Table 4.

TABLE 4

<Results of Evaluation of Pungent Smell and Eye-Smarting>

|  | First Part + Second Part | Pungent Smell | Eye-smarting |
|---|---|---|---|
| Ex. 1 | Prep. Ex. 1-1 + Prep. Ex. 2-1 | ◉ | ◉ |
| Ex. 2 | Prep. Ex. 1-1 + Prep. Ex. 2-2 | ○ | ○ |
| Ex. 3 | Prep. Ex. 1-2 + Prep. Ex. 2-1 | ○ | ○ |
| Ex. 4 | Prep. Ex. 1-2 + Prep. Ex. 2-2 | Δ | ○ |
| Ex. 5 | Prep. Ex. 1-3 + Prep. Ex. 2-1 | ○ | ○ |
| Ex. 6 | Prep. Ex. 1-4 + Prep. Ex. 2-1 | ○ | Δ |
| Ex. 7 | Prep. Ex. 1-5 + Prep. Ex. 2-1 | ◉ | ◉ |
| Ex. 8 | Prep. Ex. 1-5 + Prep. Ex. 2-2 | ◉ | ◉ |
| Ex. 9 | Prep. Ex. 1-6 + Prep. Ex. 2-1 | ○ | ○ |
| Ex. 10 | Prep. Ex. 1-6 + Prep. Ex. 2-2 | ○ | ○ |
| Ex. 11 | Prep. Ex. 1-7 + Prep. Ex. 2-1 | ○ | ○ |
| Ex. 12 | Prep. Ex. 1-8 + Prep. Ex. 2-1 | Δ | ○ |
| Comp. Ex. 1 | Prep. Ex. 1-3 + Prep. Ex. 2-2 | X | X |
| Comp. Ex. 2 | Prep. Ex. 1-4 + Prep. Ex. 2-2 | X | X |
| Comp. Ex. 3 | Prep. Ex. 1-7 + Prep. Ex. 2-2 | X | X |
| Comp. Ex. 4 | Prep. Ex. 1-8 + Prep. Ex. 2-2 | X | X |

<Evaluation Criteria>

◉: good, ○: medium, Δ: poor, ×: absolutely poor

As shown in Table 4, it can be seen that Examples using an ether type nonionic surfactant (polyethylene oxide stearyl ether), ether type oil (polypropylene oxide stearyl ether) and a higher alcohol (cetearyl alcohol, cetyl alcohol) having the same carbon number provide a reduced degree of pungent smell and eye-smarting as compared to Comparative Examples not using at least one of the three ingredients.

Test Example 3

Evaluation of Stability

Each of the first part compositions 1-9 to 1-20 is prepared according to the ingredients and amounts as shown in the following Table 5 and Table 6.

TABLE 5

| Ingredients | Preparation Example of First Part (wt %) | | | | | |
|---|---|---|---|---|---|---|
|  | 1-9 | 1-10 | 1-11 | 1-12 | 1-13 | 1-14 |
| Cetearyl alcohol | 3.0 | 3.0 | 3.0 | 3.0 | 3.0 | 3.0 |
| Polyethylene oxide oleyl ether (EO: 30 mole) | 1.0 | — | — | — | 1.0 | — |
| Polyethylene oxide stearyl ether (EO: 21 mole) | — | 1.0 | — | — | — | 1.0 |
| Polyethylene oxide cetearyl ether (EO: 30 mole) | — | — | 1.0 | — | — | — |
| Polyethylene oxide lauryl ether (EO: 23 mole) | — | — | — | 1.0 | — | — |
| Polyethylene oxide lauryl ether (EO: 2 mole) | 1.0 | 1.0 | 1.0 | 1.0 | — | — |
| Polyethylene oxide oleyl ether (EO: 2 mole) | — | — | — | — | 1.0 | 1.0 |
| Polyethylene oxide stearyl ether (EO: 2 mole) | — | — | — | — | — | — |
| Polypropylene oxide stearyl ether | 0.5 | 0.5 | 0.5 | 0.5 | 0.5 | 0.5 |
| Disodium EDTA | 0.2 | 0.2 | 0.2 | 0.2 | 0.2 | 0.2 |
| Erythorbic acid | 0.4 | 0.4 | 0.4 | 0.4 | 0.4 | 0.4 |
| Sodium sulfite | 0.4 | 0.4 | 0.4 | 0.4 | 0.4 | 0.4 |
| p-phenylene diamine | 0.3 | 0.3 | 0.3 | 0.3 | 0.3 | 0.3 |
| m-aminophenol | 0.3 | 0.3 | 0.3 | 0.3 | 0.3 | 0.3 |
| p-aminophenol | 0.3 | 0.3 | 0.3 | 0.3 | 0.3 | 0.3 |
| Resorcinol | 0.3 | 0.3 | 0.3 | 0.3 | 0.3 | 0.3 |

TABLE 5-continued

| | Preparation Example of First Part (wt %) | | | | | |
|---|---|---|---|---|---|---|
| Ingredients | 1-9 | 1-10 | 1-11 | 1-12 | 1-13 | 1-14 |
| Ethanolamine | 5.0 | 5.0 | 5.0 | 5.0 | 5.0 | 5.0 |
| Combined fragrance | qsad | qsad | qsad | qsad | qsad | qsad |
| Purified water | to 100 | to 100 | to 100 | to 100 | to 100 | to 100 |

TABLE 6

| | Preparation Example of First Part (wt %) | | | | | |
|---|---|---|---|---|---|---|
| Ingredients | 1-15 | 1-16 | 1-17 | 1-18 | 1-19 | 1-20 |
| Cetearyl alcohol | 3.0 | 3.0 | 3.0 | 3.0 | 3.0 | 3.0 |
| Polyethylene oxide oleyl ether (EO: 30 mole) | — | — | 1.0 | — | — | — |
| Polyethylene oxide stearyl ether (EO: 21 mole) | — | — | — | 1.0 | — | — |
| Polyethylene oxide cetearyl ether (EO: 30 mole) | 1.0 | — | — | — | 1.0 | — |
| Polyethylene oxide lauryl ether (EO: 23 mole) | — | 1.0 | — | — | — | 1.0 |
| Polyethylene oxide lauryl ether (EO: 2 mole) | — | — | — | — | — | — |
| Polyethylene oxide oleyl ether (EO: 2 mole) | 1.0 | 1.0 | — | — | — | — |
| Polyethylene oxide stearyl ether (EO: 2 mole) | — | — | 1.0 | 1.0 | 1.0 | 1.0 |
| Polypropylene oxide stearyl ether | 0.5 | 0.5 | 0.5 | 0.5 | 0.5 | 0.5 |
| Disodium EDTA | 0.2 | 0.2 | 0.2 | 0.2 | 0.2 | 0.2 |
| Erythorbic acid | 0.4 | 0.4 | 0.4 | 0.4 | 0.4 | 0.4 |
| Sodium sulfite | 0.4 | 0.4 | 0.4 | 0.4 | 0.4 | 0.4 |
| p-phenylene diamine | 0.3 | 0.3 | 0.3 | 0.3 | 0.3 | 0.3 |
| m-aminophenol | 0.3 | 0.3 | 0.3 | 0.3 | 0.3 | 0.3 |
| p-aminophenol | 0.3 | 0.3 | 0.3 | 0.3 | 0.3 | 0.3 |
| Resorcinol | 0.3 | 0.3 | 0.3 | 0.3 | 0.3 | 0.3 |
| Ethanolamine | 5.0 | 5.0 | 5.0 | 5.0 | 5.0 | 5.0 |
| Combined fragrance | qsad | qsad | qsad | qsad | qsad | qsad |
| Purified water | to 100 | to 100 | to 100 | to 100 | to 100 | to 100 |

First, as aqueous phase, purified water, disodium EDTA (Na-EDTA), erythorbic acid, sodium sulfite, a dye, or the like are introduced, warmed to 75° C. and dissolved. In addition, as oil phase, cetearyl alcohol, polyethylene oxide stearyl ether, polypropylene oxide stearyl ether and a surfactant are introduced, warmed to 75° C. and dissolved. As shown in Tables 5 and 6, each preparation example uses different ingredients.

Next, the aqueous phase and the oil phase are mixed and emulsified, followed by cooling to 40° C. In addition, ethanolamine and a combined fragrance are further added thereto and mixed homogeneously to provide each of the first part compositions.

Finally, each composition is introduced to a PET container with LPG (propane:butane=30:70) and sealed so that the composition and LPG are mixed and filled in a weight ratio of 90-95:10-5, thereby providing an aerosol type formulation.

Figure 5:
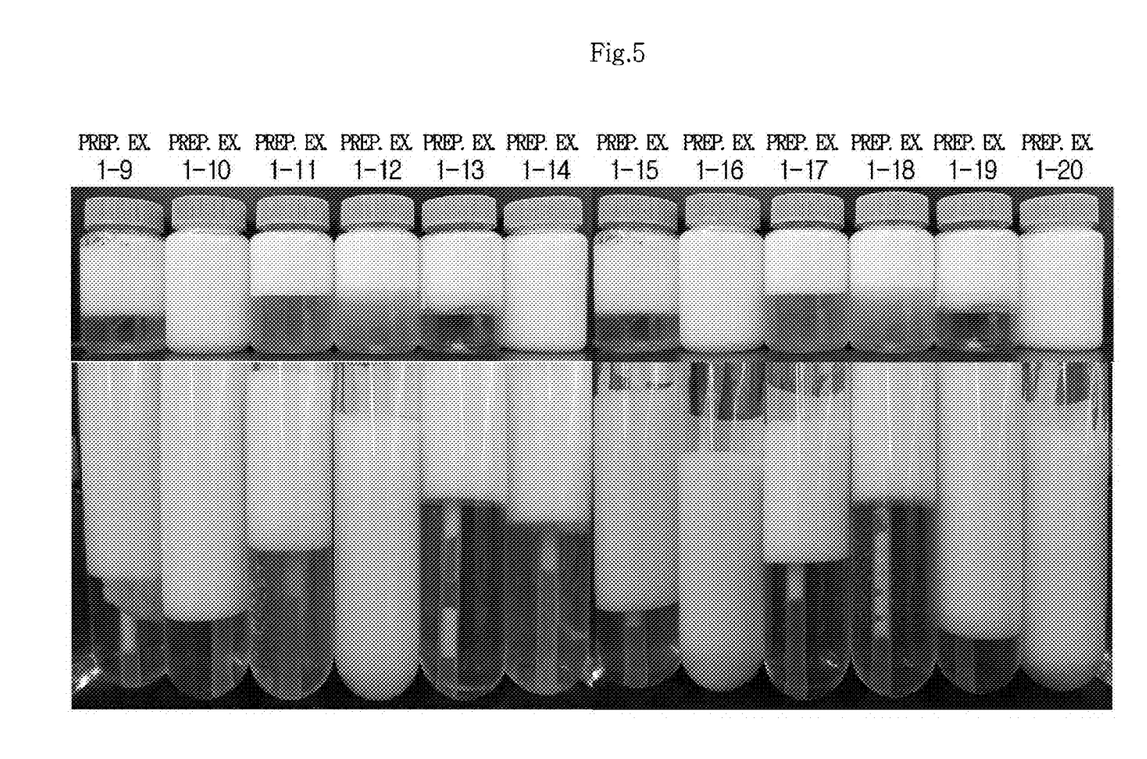
FIG. 5 is a photograph showing the stability of the first part of a dyeing composition and an aerosol type formulation comprising the same according to an embodiment of the present disclosure.

Then, each composition is observed for its stability before and after mixing with LPG, and the results are shown in FIG. 5.

As shown in FIG. 5, Preparation Examples 1-10, 1-14 and 1-18 containing polyoxyethylene stearyl ether (21 mole) show high stability. Among them, Preparation Example 1-18 containing an ether type nonionic surfactant (polyethylene oxide stearyl ether) and ether type oil (polypropylene oxide stearyl ether) having the same carbon number shows the highest stability. It is thought that the lamella structure formed by such an ether type nonionic surfactant and ether type oil having the same carbon number improves the stability of a composition and allows LPG to be supported efficiently in the inner phase.

The invention claimed is:

1. A dyeing composition, comprising:
   an ether type nonionic surfactant;
   ether type oil; and
   an alcohol, wherein the ether type nonionic surfactant, ether type oil and the alcohol have the same carbon number as each other,
   wherein the dyeing composition further comprises a phosphate surfactant,
   wherein the ether type nonionic surfactant, ether type oil and the alcohol form a multi-lamella liquid crystal structure,
   wherein the dyeing composition has a pH of 7-12,
   wherein the ether type nonionic surfactant is selected from ethylene oxide-containing surfactants, and comprises at least two surfactants having a different ethylene oxide mole number.

2. The dyeing composition according to claim 1, which comprises a first part comprising an oxidative dye precursor, coupler and an alkaline agent, and a second part comprising an oxidizing agent, wherein the ether type nonionic surfactant, ether type oil and the alcohol are comprised to at least one part selected from the first part and the second part.

3. The dyeing composition according to claim 1, wherein the ether type nonionic surfactant comprises a polyethylene oxide stearyl ether having an ethylene oxide (EO) mole number equal to or more than 0.2 moles and less than 10 moles, and a polyethylene oxide stearyl ether having an ethylene oxide (EO) mole number of 10 moles or more and 40 moles or less.

4. The dyeing composition according to claim 1, wherein the ether type nonionic surfactant is polyethylene oxide alkyl ether.

5. The dyeing composition according to claim 1, wherein the ether type nonionic surfactant is selected from at least two surfactants, and comprises a surfactant having an HLB less than 10 and another surfactant having an HLB of 10 or more.

6. The dyeing composition according to claim 5, wherein the ether type nonionic surfactant comprises a surfactant having an HLB less than 10 and another surfactant having an HLB of 10 or more in a weight ratio of 2-2.5:1-1.5.

7. The dyeing composition according to claim 1, wherein the ether type oil is polypropylene oxide alkyl ether.

8. The dyeing composition according to claim 1, which has a formulation of solution, emulsion, cream, suspension, solid, gel, powder, paste, foam or aerosol.

9. The dyeing composition according to claim 8, wherein the aerosol formulation comprises a spraying agent.

10. The dyeing composition according to claim 9, wherein the spraying agent is at least one selected from propane gas, butane gas and mixed propane/butane gas, and dimethyl ether.

* * * * *